US006730912B2

(12) United States Patent
Sun et al.

(10) Patent No.: US 6,730,912 B2
(45) Date of Patent: May 4, 2004

(54) METHOD AND APPARATUS FOR DETECTING NORMAL CRACKS USING INFRARED THERMAL IMAGING

(75) Inventors: Jiangang G. Sun, Westmont, IL (US); Scott M. Erdman, Palos Hills, IL (US)

(73) Assignee: The University of Chicago, Chicago, IL (US)

( * ) Notice: Subject to any disclaimer, the term of this patent is extended or adjusted under 35 U.S.C. 154(b) by 77 days.

(21) Appl. No.: 10/232,176

(22) Filed: Aug. 30, 2002

(65) Prior Publication Data

US 2004/0041096 A1 Mar. 4, 2004

(51) Int. Cl.$^7$ ............................................. G01N 25/72
(52) U.S. Cl. ................................. 250/341.6; 250/341.1
(58) Field of Search ............................ 250/338.1, 340, 250/341.1, 341.6

(56) References Cited

U.S. PATENT DOCUMENTS

| | | | |
|---|---|---|---|
| 4,826,326 A | 5/1989 | Reynolds et al. | |
| 5,689,332 A | 11/1997 | Ellingson et al. | |
| 5,711,603 A | 1/1998 | Ringermacher et al. | |
| 5,719,395 A | * 2/1998 | Lesniak | 250/330 |

OTHER PUBLICATIONS

"Front–Flash Thermal Imaging Characterization of Continuous Fiber Ceramic Composites", C. Deemer et al., 23rd Annual Cocoa Beach Conf. & Exposition: An Int. Conf. On Engineering Ceramics (1999).

Early–Timpe Pulse–Echo Thermal Wave Imaging, X. Han et al., Review in Progress in QNDE, vol. 15, pp. 519–524, (1996).

"Nondestructive Evaluation of Materials by Infrared Thermography", X. Maldague, Springer, London, (1993).

"Pulse phase infrared thermography", X. Maldague et al., J. Appl. Phys., 79(5), pp. 2694–2698 (1996).

"Flash method of determining thermal diffusivity, heat capacity, and thermal conductivity", W. J. Parker et al., J. Appl. Phys., 32(1), pp. 1679–1684 (1961).

"Thermal Imaging Measurement and Correlation of Thermal Diffusivity in Sontinuous Fiber Ceramic Composites", J. G. Sun et al, Thermal Conductivity 24, eds. P.S. Gall et al., pp. 616–622 (1999).

* cited by examiner

*Primary Examiner*—Constantine Hannaher
*Assistant Examiner*—Timothy Moran
(74) *Attorney, Agent, or Firm*—Joan Pennington

(57) ABSTRACT

A method and infrared thermal imaging apparatus detects normal and angled cracks on or beneath a sample surface using infrared thermal imaging where the crack plane is perpendicular or angled to an imaged surface of the sample. A constant heating source is used for heating a section of the sample to produce a lateral heat transfer through the sample. An infrared camera is positioned near one side of the sample for receiving thermal image data resulting from the lateral heat transfer through the sample. A data acquisition and processing computer is used for acquiring and differentiation processing thermal image data from the infrared camera for generating two-dimensional first derivative and second derivative images to detect the normal and angled cracks.

14 Claims, 20 Drawing Sheets d/L = 0.25 d/L = 0.5 d/L = 0.75 d/L = 0.25 d/L = 0.5 d/L = 0.75

$(\partial T / \partial x)/Tm$ $(\partial T / \partial x)/Tm$ $(\partial T/\partial x)/Tm$ d/L = 0.025 d/L = 0.25 d/L = 0.75 d/L = 0.25 d/L = 0.75 d/L = 0.25 d/L = 0.5 d/L = 0.75 d/L = 0.5 d/L = 0.75

METHOD AND APPARATUS FOR DETECTING NORMAL CRACKS USING INFRARED THERMAL IMAGING

CONTRACTUAL ORIGIN OF THE INVENTION

The United States Government has rights in this invention pursuant to, Contract No. W-31-109-ENG-38 between the United States Government and Argonne National Laboratory.

FIELD OF THE INVENTION

The present invention relates to a method and apparatus for detecting normal and angled cracks on or beneath a surface using infrared thermal imaging where the crack plane is perpendicular to or has a perpendicular component to an imaged surface.

DESCRIPTION OF THE RELATED ART

Normal cracks in which the crack plane is perpendicular to the surface are major safety and reliability concerns for structural components used in airplanes, automobiles, pipes in nuclear reactor systems, and others. Normal surface breaking and subsurface cracks, for example, resulting from fatigue at locations of high stress concentrations and from corrosion in pipes in nuclear power plant piping, are not effectively detected by known nondestructive testing techniques. Considerable research and development works have and are still being devoted for detecting and characterizing these cracks.

Most of the current developments utilize ultrasonic techniques. Depending on the configurations of the cracks, various ultrasonic systems can be used. For example, angled ultrasonic waves can be used for detecting internal cracks, and surface waves for surface breaking cracks. This type of techniques typically requires contact scanning of sample to obtain information of crack distribution which may be difficult for components of complex geometry and the testing is usually time consuming.

Infrared thermal imaging, traditionally known as thermography, is becoming widely used in nondestructive detection of defects in components such as developed by Jiangang Sun, Chris M. Deemer, and William A. Ellingson. Most thermal imaging techniques are based upon applying flash heating on a sample surface, then monitoring the decay of the surface temperature by an infrared camera. Defects on or under the surface can then be found from the thermal images of the surface because defects have different thermal resistance than the sample material and therefore affect the decay rate of the local surface temperature. Depending on the direction of heat transfer, lateral cracks in which the crack plane is parallel to the sample surface are easily determined by applying instantaneous uniform heating on the entire surface, while a single normal crack can be determined by applying the same heating on only one side of the crack, but requires prior knowledge of the crack direction to be aligned with experimental setup and can only characterize one crack at a time.

Recently a new hybrid ultrasonic/thermal-imaging technique called ThermoSonix was developed by Indigo Systems to detect cracks in a component. In this hybrid ultrasonic/thermal-imaging technique, a short pulse of ultrasound energy is applied to a component, which causes frictional heating at crack surfaces that may reach to the surface monitored by an infrared camera. This technique can detect cracks of all orientations. The technique is based on the frictional heating between the two interfaces of a tight crack so frictional heating can be generated from the two surfaces on either side of the cracks. However, the frictional heating does not exist when the crack surfaces are separated by a small gap in open cracks whose two side surfaces are not in contact. Such open cracks are more severe but cannot be detected by this technique.

Known techniques cannot reliably detect and accurately characterize a distribution of normal cracks. Known nondestructive evaluation (NDE) techniques cannot reliably detect and accurately characterize cracks normal to the surface in ceramic materials.

A principal object of the present invention is to provide a method and infrared thermal imaging apparatus for detecting normal and angled cracks on or beneath a surface where the crack plane is perpendicular to or has a perpendicular component to an imaged surface.

It is another object of the invention to provide such method and infrared thermal imaging apparatus for detecting normal and angled cracks on or beneath a surface that is generally fast, and accurate.

It is another object of the invention to provide such method and infrared thermal imaging apparatus for detecting normal and angled cracks on or beneath a surface for automated non-destructive evaluation (NDE) thermal imaging of samples formed of various materials and that is not dependent on material properties.

It is another object of the invention to provide such method and infrared thermal imaging apparatus for detecting normal and angled cracks on or beneath a surface substantially without negative effect and that overcome many of the disadvantages of prior arrangements.

SUMMARY OF THE INVENTION

In brief, a method and infrared thermal imaging apparatus are provided for detecting normal and angled cracks on or beneath a sample surface using infrared thermal imaging where the crack plane is perpendicular to or has a perpendicular component to an imaged surface of the sample. A constant heating source is used for heating a section of the sample to produce a lateral heat transfer through the sample. An infrared camera is positioned near one side of the sample for receiving thermal image data resulting from the lateral heat transfer through the sample. A data acquisition and processing computer is used for acquiring and differentiation processing thermal image data from the infrared camera for generating a two-dimensional image to detect the normal and angled cracks.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
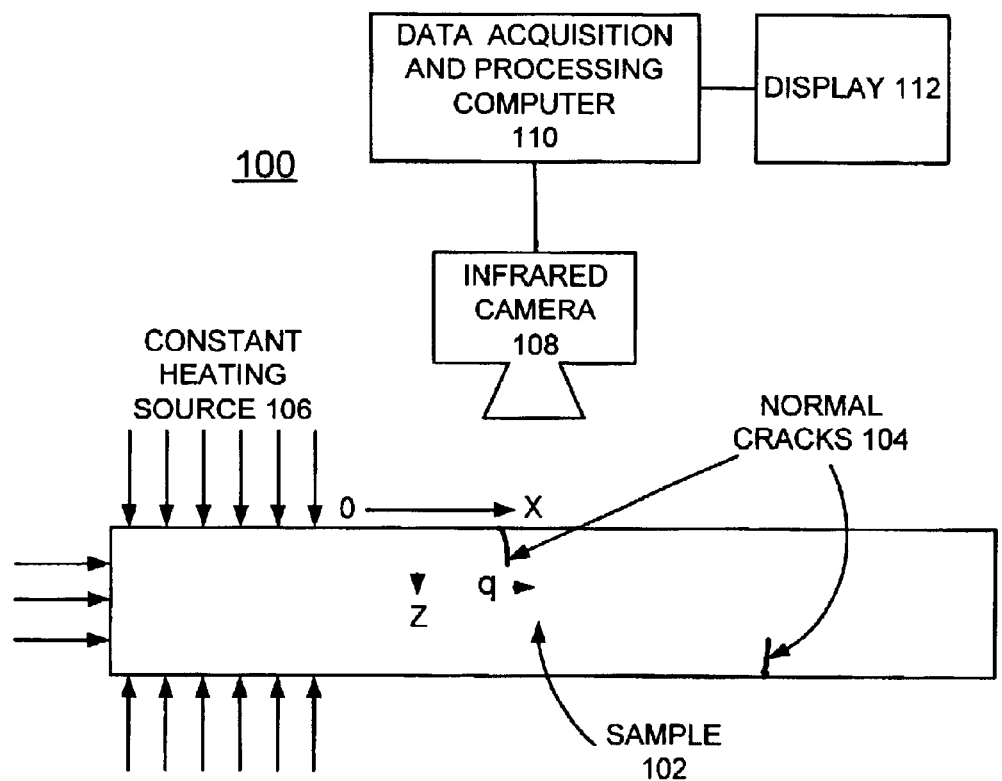
FIG. 1 is a diagram illustrating a thermal imaging apparatus for implementing a method for detecting and characterizing multiple normal and angled cracks on or beneath a sample surface in accordance with the preferred embodiment.

Having reference now to the drawings, FIG. 1 illustrates a thermal imaging apparatus generally designated by the reference numeral 100 for detecting and characterizing multiple normal and angled cracks on or beneath a sample surface in accordance with the preferred embodiment. A plate sample 102 having a pair of normal cracks 104 is illustrated in FIG. 1. Thermal imaging system 100 includes a constant heating source 106 for heating a section of the sample 102 to provide a thermal energy flow or heat flow indicated by q along an X direction through the sample. Thermal imaging system 100 includes a high-resolution and high-sensitivity infrared camera 108, for example, with 256×256 pixel focal plane array of infrared sensors. Infrared camera 108 is positioned on one side of the sample 102 for obtaining thermal data from the sample portion receiving lateral thermal energy flow or lateral heat flow as indicated by q along an X direction through the sample. A data acquisition and processing computer 110 is coupled the infrared camera 108 for first and second derivative data processing of measured temperature data from the infrared camera and displaying two dimensional first and second derivative data image results on an associated display 112.

The present invention provides a new method for accurately detecting and characterizing multiple normal and angled cracks on or beneath a sample surface using the infrared thermal imaging apparatus 100. Rather than flash heating a surface, the constant heat source 106 is used to heat a section of the sample 104 to establish a lateral heat transfer through the sample. The principle of the technique is based on the higher thermal resistance of a crack, typically filled with air, to reduce heat transfer across the crack plane so a low temperature region will be formed behind the crack and detected by the thermal imaging apparatus 100. However, the temperature drop across a crack could be small so difficult to identify. The transient thermal-imaging data are processed to enhance the cracks and the result is presented as a two-dimensional (2D) surface image showing the distribution of cracks whose depth can be correlated with the crack-feature intensity in the image. The technique can be used for samples of various configurations and formed of various materials including metallic and non-metallic materials. A direct application of this technique is in nondestructive evaluation (NDE) of defects and fatigue cracks found in aging aircraft components, automobile components, and nuclear reactor pipes, and the like.

Thermal imaging apparatus 100 is used for normal crack detection within the sample 102 for a cross section (x-z plane) of the sample plate that includes two normal cracks 104, as shown in FIG. 1. It is assumed that temperature variation in the other third direction (y direction) perpendicular to the x-z plane is small so a two-dimensional (2D) heat transfer condition is illustrated with constant heating source 106. The sample plate 102 is initially at ambient temperature $T_0$, and is heated at the left side (x<0) provided by heating source 106 of constant higher temperature $T_1$ or heat flux at time t=0. There are several options for applying the heat source 106, for example, as illustrated in FIGS. 3A, 3B, and 3C.

Figure 3A:
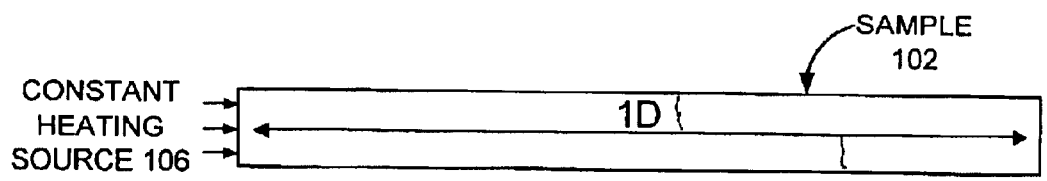
FIGS. 3A, 3B, and 3C illustrate alternative constant heating source configurations and heat conduction effects in a sample plate.
Figure 3B:
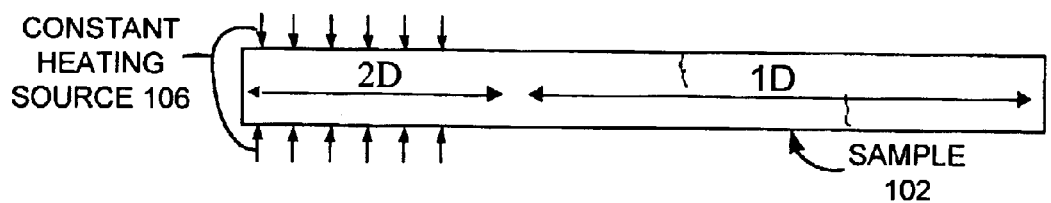
Figure 3C:
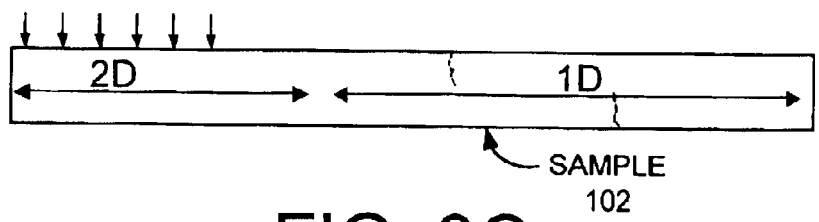

Referring to FIGS. 3A, 3B, and 3C, constant heating is applied at the end of the plate as shown in FIG. 3A; a pure one-dimensional (1D) heat conduction (in the X direction) is generated for a uniform plate having no cracks. If the heat source is applied on one or both surfaces, such as resistance conductor heating, of the plate 102 as shown in FIGS. 3B and 3C, two-dimensional (2D) heat conduction exists within a short distance from the heat source 106, as indicated by arrow labeled 2D, which typically a value of a few times of the plate thickness. Beyond this region, the heat conduction is essentially 1D, as indicated by arrow labeled 1D. However, the 1D heat conduction assumption, although easily achievable, is not necessary for detecting cracks by this invention, but it helps in explanation of the theory and interpretation of data and becomes necessary only when needed to determine additional material properties such as thermal diffusivity.

For 1D heat conduction in a plate as illustrated in FIG. 1, the transient heat conduction equation is represent by the following equation 1:

$$\frac{\partial T}{\partial t} = \alpha \frac{\partial^2 T}{\partial x^2}, \quad (1)$$

where $\alpha$ is the thermal diffusivity. The heat flux q along the x direction is defined by the following equation 2:

$$q = -k \frac{\partial T}{\partial x}, \quad (2)$$

where k is the thermal conductivity ($k=\alpha \rho c_p$, with $\rho$ the density and $c_p$ the specific heat), and q is positive in the positive x direction. Note that in equation 2 no distinction is made between local or cross-sectional averaged heat flux for simplicity. Equation 2 provides the basic formulation for crack detection, and equation 1 is the formulation for determining thermal diffusivity.

Figure 2A:
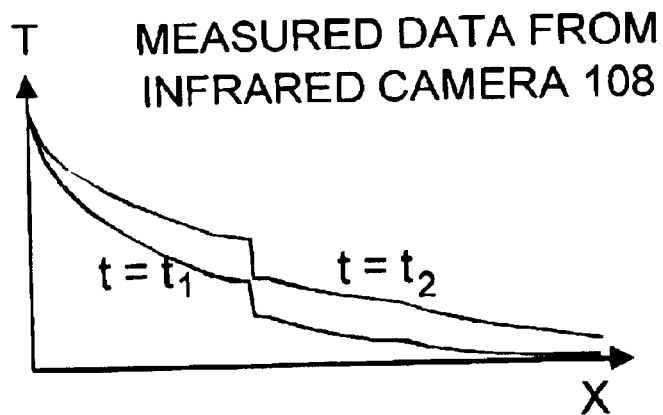
FIG. 2A is a chart illustrating two typical temperature distribution on the top surface of a sample plate at times t1 and t2 in accordance with the preferred embodiment with temperature shown with respect to a vertical axis and distance x along a horizontal.
Figure 2B:
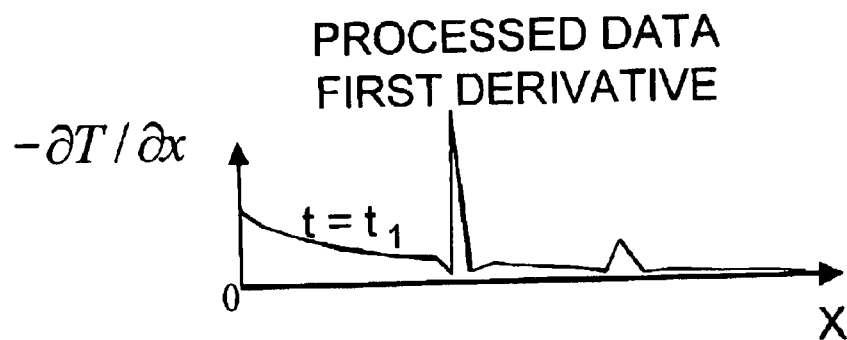
FIG. 2B is a chart illustrating crack detection in accordance with the preferred embodiment with first $-\partial T/\partial x$ shown respect to a vertical axis and distance x along a horizontal axis.
Figure 2C:
FIG. 2C is a chart illustrating transient heat conduction in accordance with the preferred embodiment with $(\partial T/\partial t)/(\partial^2 T/\partial x^2)$ shown respect to a vertical axis and distance x along a horizontal axis in accordance with the preferred embodiment.

Referring to FIGS. 2A, 2B, and 2C, thermal image processing in accordance with the present invention may be understood. FIG. 2A illustrates two typical temperature distributions on the top surface of the sample plate 102 at times $t_1$ and $t_2$, where $t_2 > t_1$. In regions without cracks, the temperature decreases gradually along x. However, if a normal crack exists which is filled with air of typically much smaller k, a temperature drop can be observed across the crack. The temperature drop is more apparent if the crack is open on the surface and milder if the crack is deep beneath the surface. This temperature drop is usually small compared with the large temperature range induced by the transient heat transfer and can be difficult to be observed directly from experimental temperature distribution data in the presence of noise.

FIG. 2B plots processed first derivative data representing the $-\partial T/\partial x$ distribution along the x direction derived from one temperature curve illustrated in FIG. 2A. It is apparent that the temperature drop across the crack is enhanced and the gradual temperature variation in the uniform material regions is suppressed. The $-\partial T/\partial x$ plot along x-direction not only shows positions of the cracks, but also contains information for the configuration of the cracks, such as crack length in depth, crack distance from the surface. When $-\partial T/\partial x$ curves are calculated at all x-lines (i.e., at each y=constant lines assuming the sample surface is on x-y plane), then a two-dimensional $-\partial T/\partial x$ image can be obtained which will, in addition, show the length and distribution of cracks extending on the sample surface. This 2D-$\partial T/\partial x$ image is the basic result of this invention for crack detection and characterization. Note that to detect normal cracks aligned perpendicular to x direction; a 2D $-\partial T/\partial y$ image should be measured.

We can further process the temperature-distribution data to plot $(\partial T/\partial t)/(\partial^2 T/\partial x^2)$ provided the noise in the data is relatively small. Based on Equation 1, this plot provides thermal diffusivity $\alpha$ along x direction for pure 1D heat conduction cases. Small errors will be present in predicted $\alpha$ if 1D heat conduction condition is not established in the plate or sample 102.

FIG. 2C illustrates the $(\partial T/\partial t)/(\partial^2/\partial x^2)$ curve along x direction derived from the two temperature curves shown in FIG. 2A. The curve is complex at the crack region. However, for uniform material, that is no cracks, of varying diffusivity, this measurement can determine thermal diffusivity variation along the sample plate 102.

Figure 4A:
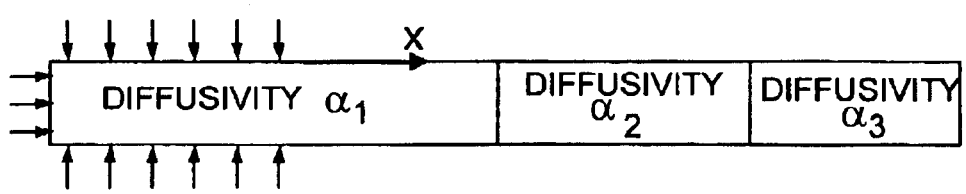
FIGS. 4A and 4B respectively illustrate a sample plate with three diffusivity regions and second derivative processed data for the example of FIG. 4A in accordance with the preferred embodiment.
Figure 4B:
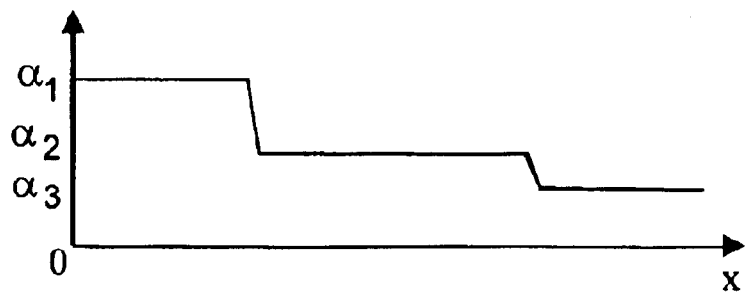

Referring to FIGS. 4A and 4B measuring thermal diffusivity of a sample plate in accordance with the present invention is illustrated. FIG. 4A illustrates an example sample plate with three jointed materials of different thermal diffusivities indicated by $\alpha 1$, $\alpha 2$, and $\alpha 3$. FIG. 4B illustrates the expected second derivative processed data or $(\partial T/\partial t)/(\partial^2 T/\partial x^2)$ plot, where $\alpha 1 > \alpha 2 > \alpha 3$ for the illustrated example.

Figure 5:
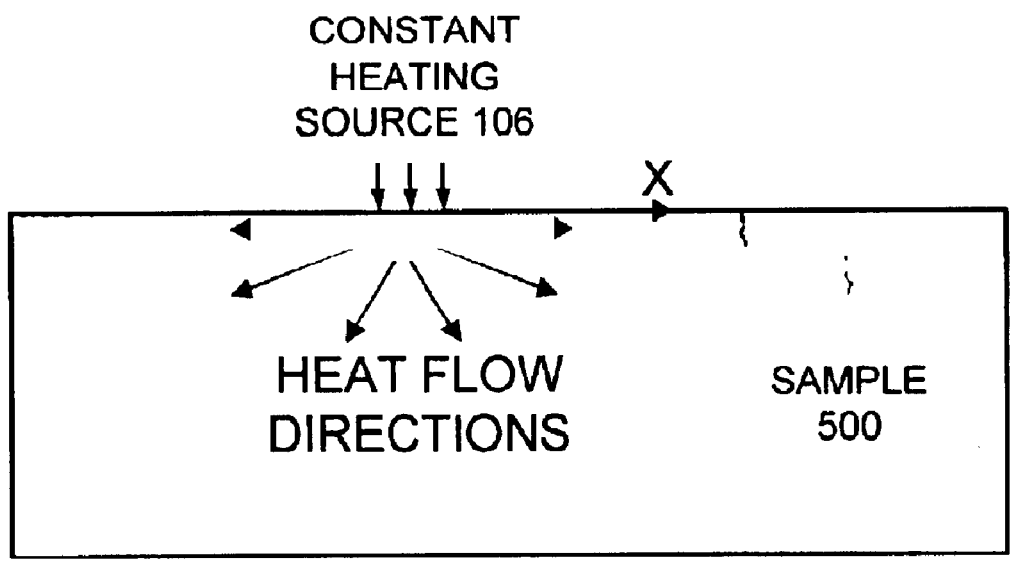
FIG. 5 is a diagram illustrating heat conduction in a thick sample.

Referring to FIG. 5, a thick sample generally designated by 500 is shown. For thick samples with a surface heating source as illustrated in FIG. 5, heat flows in all directions in the x-z plane indicated by multiple arrows labeled HEAT FLOW DIRECTIONS, resulting in a steeper decrease of temperature along the x-direction as compared for a relatively thin plate, for example, as shown in FIG. 1. Under this condition, the 2D $-\partial T/\partial x$ image is still useful to identify cracks. The $(\partial T/\partial t)/(\partial^2 T/\partial x^2)$ image is less meaningful to be interpreted as thermal diffusivity data.

In operation, experimental temperature-distribution data are obtained by using infrared thermal imaging apparatus 100. Infrared camera 108 is focused to view a sample surface of interest, and heat source 106 is applied to generate a 1D heat conduction within the sample 102. The heat source 106 can be a pool of boiling water that has a constant temperature of 100° C., a resistor heating element, a heat flux unit such as a lamp or the like. The temperature variation on the sample surface is then monitored by the camera 108 that takes a series of thermal images (temporal data) to be stored in the computer 110 for data processing. Each image contains a 2D array of pixels (spatial data). A state-of-the-art infrared camera can be used for infrared camera 108, for example, having a focal-plane-array of 256×256-pixel infrared sensors, each may convert the observed infrared energy in a particular wavelength range (e.g., 3–5 $\mu$m) to a digital value within a 12-bit dynamic range (i.e., signal value between 0 and 4095). By proper normalization of the infrared camera 108, the infrared signal values are proportional to the surface temperature.

The spatial-temporal thermal-imaging data are processed to produce a 2D $-\partial T/\partial x$ image and a 2D $(\partial T/\partial t)/(\partial^2 T/\partial x^2)$ image. In theory, one thermal image is required to calculate a $-\partial T/\partial x$ image and two thermal images for a $(\partial T/\partial t)/(\partial^2 T/\partial x^2)$ image. The additional thermal images, for example, up to or more than 100, are used to average the data to reduce random noises.

Figures 6A, 6B:
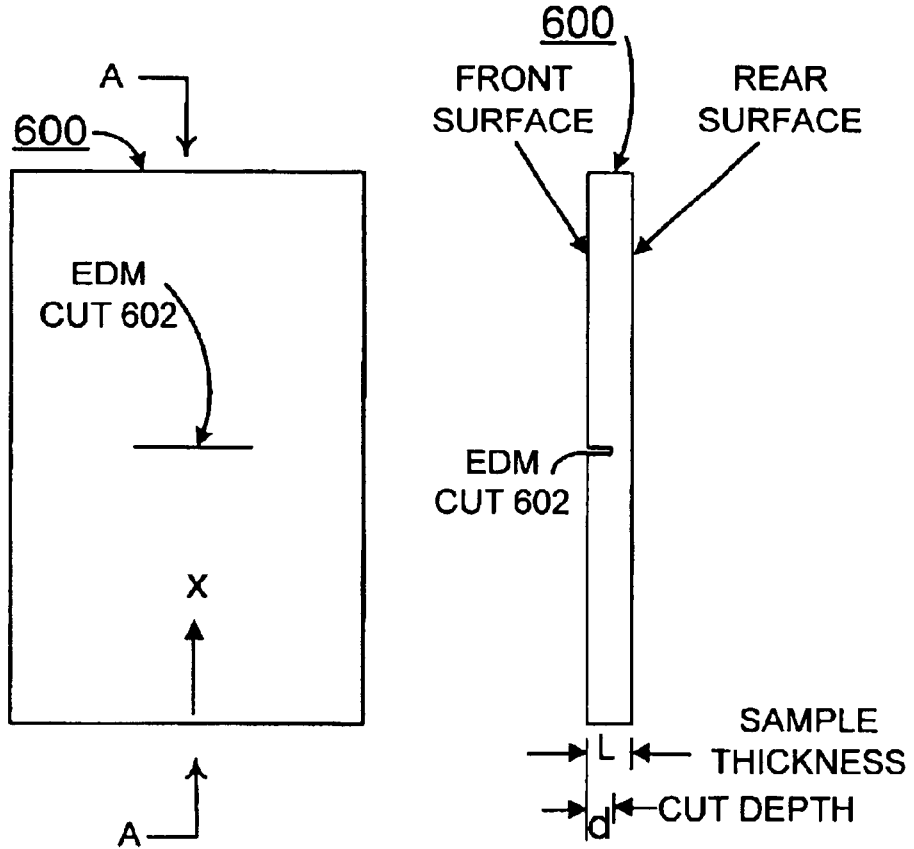
FIGS. 6A and 6B are a top view and a sectional view taken along line A—A in FIG. 6B illustrating a sample plate having an EDM cut, normal defect at a plate center along an X direction on the front surface of the sample plate.

Referring to FIGS. 6A and 6B, there is shown a sample plate 600 having an EDM cut, normal defect 602 used for theoretical calculations and experiments in accordance with the thermal imaging method for determining defect depth of the preferred embodiment. Steel-plate samples 600 are used to establish the crack-detection sensitivity of the thermal imaging method of this invention. Sample plate 600 has a thickness indicated by L. The normal defect 602 is an open crack extending inwardly from the front surface of the sample plate. The defect depth is indicated by d. The plates 600 are 2-inch wide, about 3 mm thick (that is a thickness L=3 mm), and varying lengths. A normal crack 602 of a length ⅓ of the width was machined by electron-discharge machining (EDM) at various depths d (d/L=0.025, 0.25, 0.5, and 0.75) as shown in FIG. 6B. Heat conduction in the X direction is generated to detect the crack.

Figure 7A:
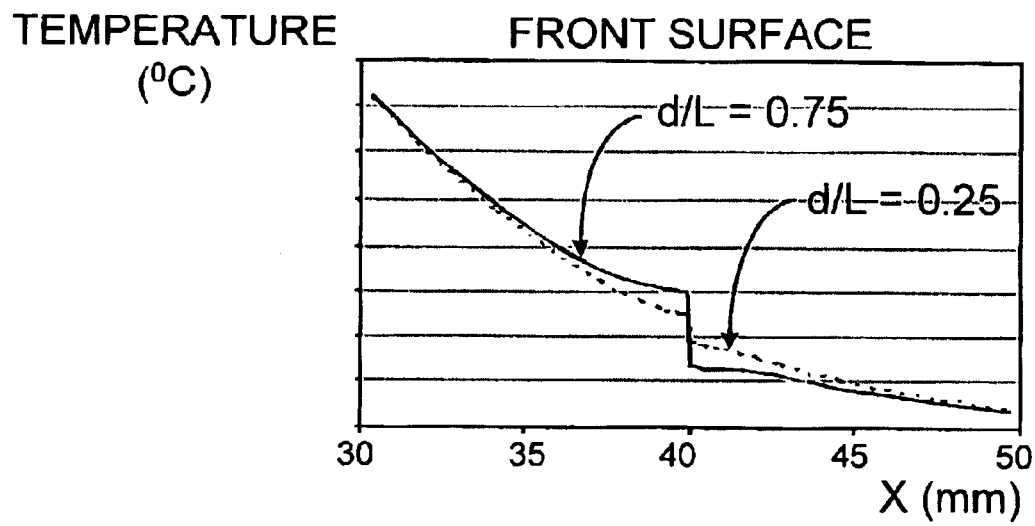
FIGS. 7A and 7B respectively illustrate computer simulaton data of thermal profiles at a plate center along an X direction on the front and back surfaces of the sample plate of FIGS. 6A and 6B in accordance with the thermal imaging method for determining defect depth of the preferred embodiment.
Figure 7B:
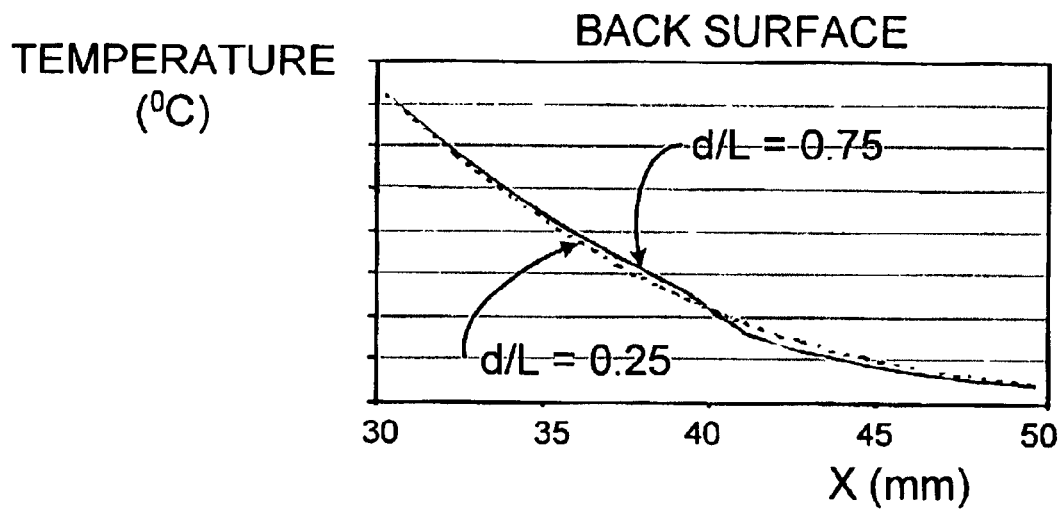

A theoretical analysis was conducted first using the illustrated sample plate 600 with normal defect 602 as shown in FIGS. 6A and 6B. Computer simulations using a COMMIX computer code developed at Argonne National Laboratory were performed to calculate the temperature distribution data that are fed into the experimental data processing software to generate detection images. The simulation assumed ideal heat conduction condition so provides ideal results (i.e., no random noises) rather than those from experiments, although there is noise due to discretization error. The plate has a geometry similar to that sample plate 600 with normal defect 602 as shown in FIGS. 6A and 6B having a thickness L of 4 mm and assumed initially at $T_0=0°$ C. A heat source at $T_1=100°$ C. is applied at one side of the plate similar to the arrangement illustrated in FIG. 3C. FIGS. 7A and 7B respectively illustrate computer simulation data of thermal profiles at a plate center along an X direction on the front and back surfaces of the sample plate 600. FIGS. 7A and 7B show the temperature distributions at front surface having the open crack 602 and back surface for cracks of depths d/L=0.25 and 0.75. On the front surface, the deeper crack (d/L=0.75) can be easily seen, but the shallower crack (d/L=0.25) is more difficult, especially when considering the total temperature variation for the entire plate is large at 100° C. (the curve plots in show only the region near the crack). On the back surface, the cracks are practically not visible.

Figure 8A:
FIGS. 8A, 8B and 8C respectively illustrate computer calculated simulations of first derivative or slope images on the front surfaces of the sample plate of FIGS. 6A and 6B at three cut depth/thickness ratios (d/L) in accordance with the thermal imaging method for determining defect depth of the preferred embodiment.
Figure 8B:
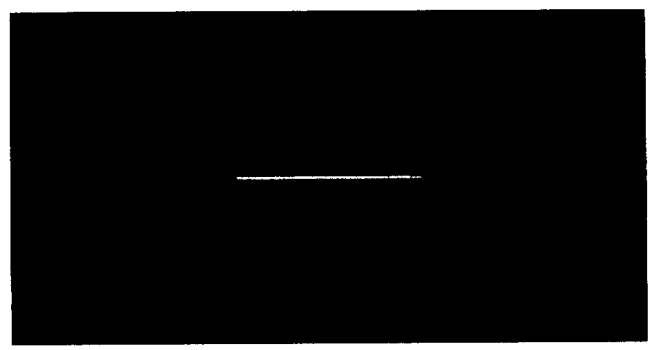
Figure 8C:

FIGS. 8A, 8B and 8C respectively illustrate computer calculated simulations of first derivative or slope images in accordance with the thermal imaging method for determining defect depth of the preferred embodiment on the front surfaces of the sample plate 600 at three cut depth/thickness ratios (d/L) of 0.25, 0.5 and 0.75. FIGS. 8A, 8B and 8C show the two-dimensional $(-\partial T/\partial x)T_m$ images or slope images from COMMIX simulations for the front surfaces, where $T_m$ is the mean local temperature.

Figure 9A:
FIGS. 9A, 9B and 9C respectively illustrate computer calculated simulations of first derivative or slope images on the back surfaces of the sample plate of FIGS. 6A and 6B at three cut depth/thickness ratios (d/L) in accordance with the thermal imaging method for determining defect depth of the preferred embodiment.
Figure 9B:
Figure 9C:

FIGS. 9A, 9B and 9C respectively illustrate computer calculated simulations of first derivative or slope images on the back surfaces of the sample plate 600 at the cut depth/thickness ratios (d/L) of 0.25, 0.5 and 0.75. In FIGS. 9A, 9B and 9C, for the back surfaces of plates with cracks d/L=0.25, 0.5, and 0.75, all cracks are clearly seen from these images.

Figure 10B:
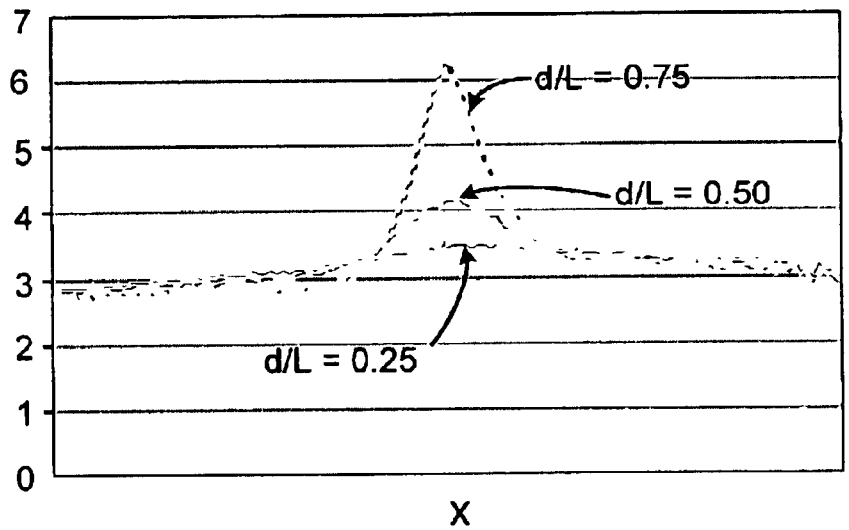
FIGS. 10A and 10B respectively illustrate computer calculated simulations of slope profiles at a plate center along an X direction on the front and back surfaces of the sample plate of FIGS. 6A and 6B from the images of FIGS. 8A, 8B and 8C and FIGS. 9A, 9B and 9C in accordance with the thermal imaging method for determining defect depth of the preferred embodiment.
Figure 10A:
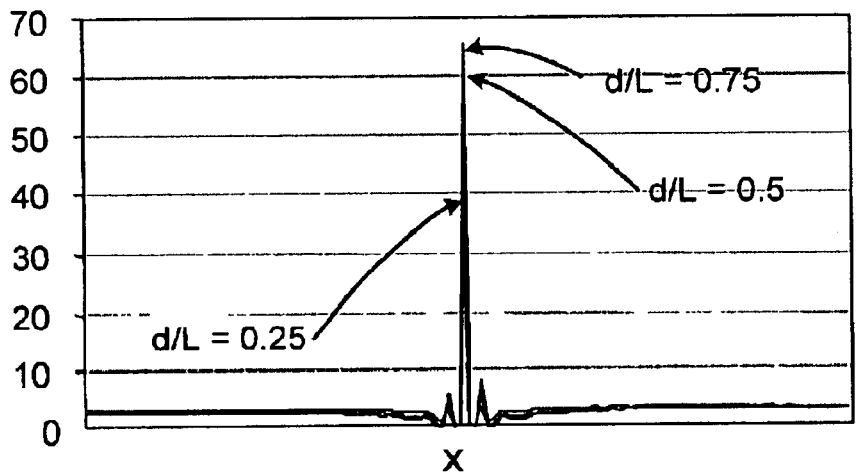

FIGS. 10A and 10B respectively illustrate computer calculated simulations of slope profiles at a plate center along an X direction on the front and back surfaces of the sample plate of 600 from the images of FIGS. 8A, 8B and 8C and FIGS. 9A, 9B and 9C in accordance with the thermal imaging method for determining defect depth of the preferred embodiment. The $(-\partial T/\partial x)T_m$ profiles are plotted in FIGS. 10A and 10B for all cracks, and it is evident that the crack detection sensitivity is very good. The magnitudes of the crack intensity in the images, however, depend on the spatial resolution of the temperature distribution data. In FIG. 10A, the curves for d/L=0.5 and d/L=0.75 are coincident at the peak (both saturated). The peak of the curves for d/L=0.75, d/L=0.5, and d/L=0.25 respectively are approximately 65, 65, and 40, as shown in FIG. 10A.

Figure 11B:
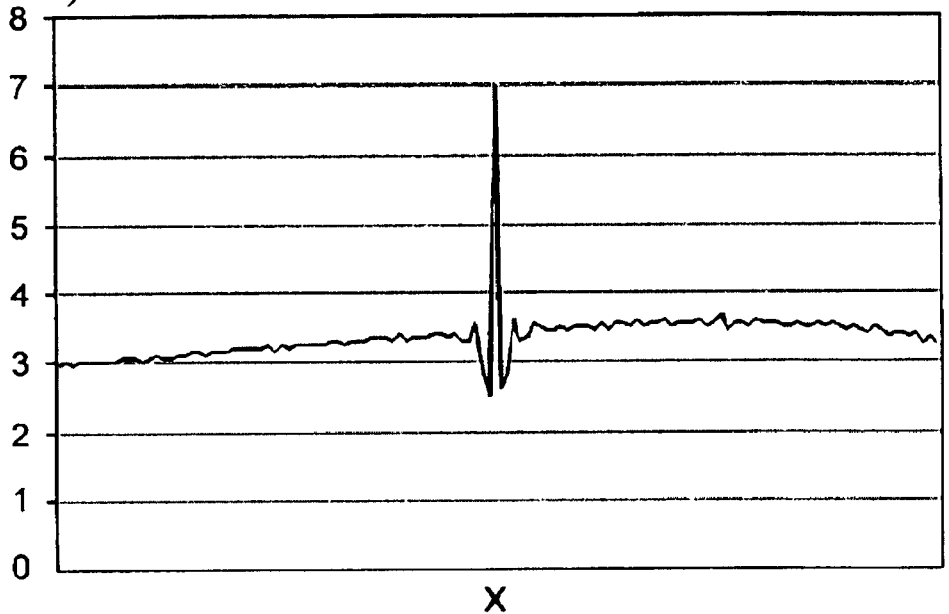
FIGS. 11A and 11B respectively illustrate computer calculated simulations of a slope image and a slope profile at a plate center along an X direction on the front surface of the sample plate of FIGS. 6A and 6B in accordance with the thermal imaging method for determining defect depth of the preferred embodiment.
Figure 11A:
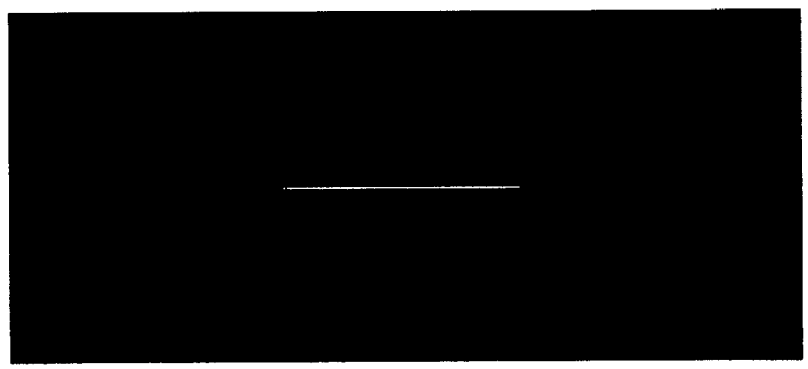

FIGS. 11A and 11B respectively illustrate computer calculated simulations of a slope image and a slope profile at a plate center along an X direction on the front surface of the sample plate 600 in accordance with the thermal imaging method for determining defect depth of the preferred embodiment. In FIGS. 11A and 11B, simulated results for a very shallow crack (d/L=0.025, or d=0.1 mm) are presented. It is evident that this crack can be detected on the crack surface by this technique.

Figure 12A:
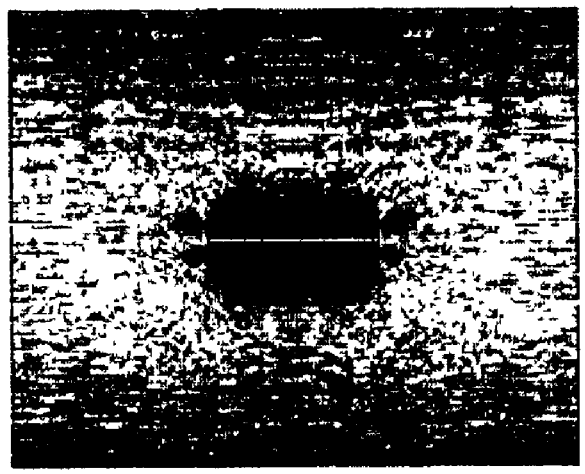
FIGS. 12A and 12B respectively illustrate computer calculated simulations of second derivative diffusivity images at a plate center along an X direction on the front surface of the sample plate of FIGS. 6A and 6B at two cut depth/thickness ratios (d/L) in accordance with the thermal imaging method for determining defect depth of the preferred embodiment.
Figure 12B:
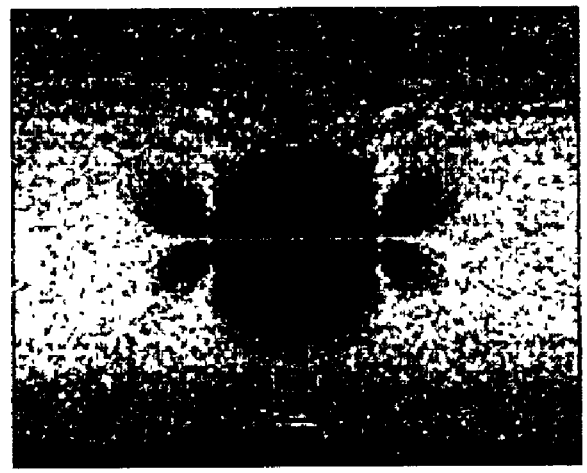
Figure 13A:
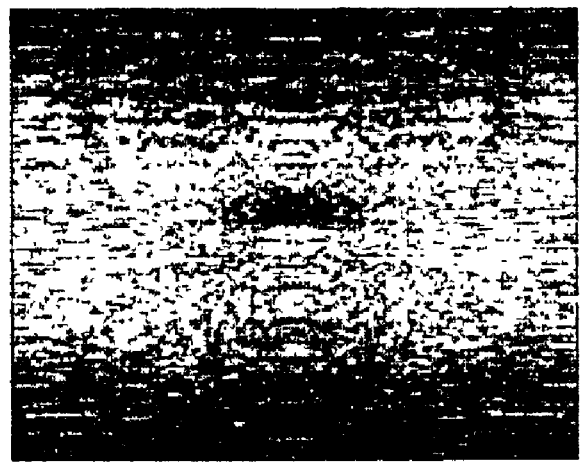
FIGS. 13A and 13B respectively illustrate computer calculated simulations of second derivative diffusivity images at a plate center along an X direction on the back surface of the sample plate of FIGS. 6A and 6B at two cut depth/thickness ratios (d/L) in accordance with the thermal imaging method for determining defect depth of the preferred embodiment.
Figure 13B:
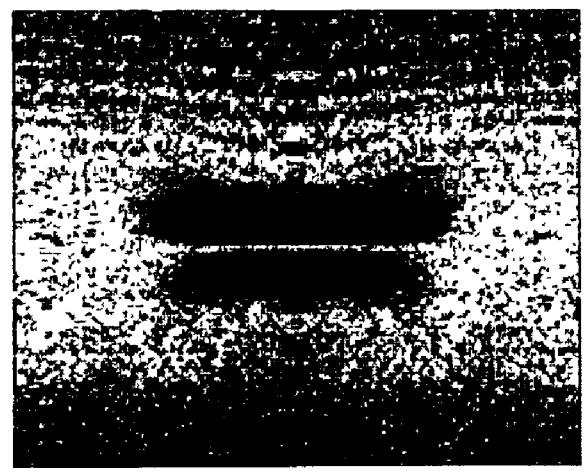

FIGS. 12A and 12B and FIGS. 13A and 13B respectively illustrate computer calculated simulations of second derivative diffusivity images in accordance with the thermal imaging method for determining defect depth of the preferred embodiment at a plate center along an X direction on the front surface and back surface of the sample plate 600 at two cut depth/thickness ratios (d/L). FIGS. 12A and 12B shows the 2D $(-\partial T/\partial t)/(\partial^2 T/\partial x^2)$ images or second derivative diffusivity images from COMMIX simulations on the front surfaces and FIGS. 13A and 13B on the back surfaces of plates with cracks depths d/L=0.25 and 0.75. The data variation near the crack is complex. The noise in the images is due to numerical discretization errors.

Referring now to FIGS. 14A, 14B, and 14C, FIGS. 15A and 15B, and FIGS. 16A, and 16B, measured experimental results are shown. In experiments, the bottom of the steel plates 600 were inserted into a pool of boiling water providing a constant heating source similar to the arrangement of constant heating source 106 as shown in FIG. 1. These experimental results are similar to those obtained from the calculated numerical simulations.

Figure 14A:
FIGS. 14A, 14B and 14C respectively illustrate experimental measured first derivative or slope images on the front surfaces of the sample plate of FIGS. 15A and 15B at three cut depth/thickness ratios (d/L) in accordance with the thermal imaging method for determining defect depth of the preferred embodiment.
Figure 14B:
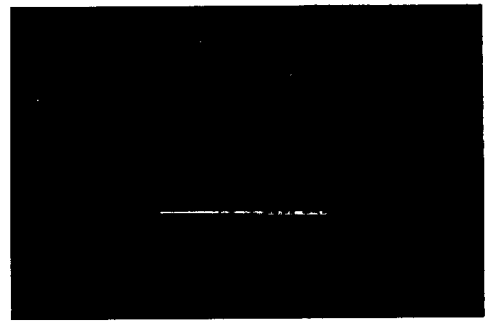
Figure 14C:
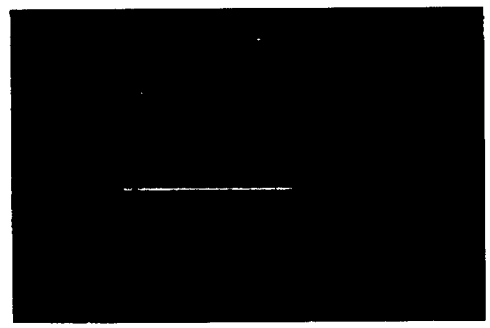
Figure 15A:
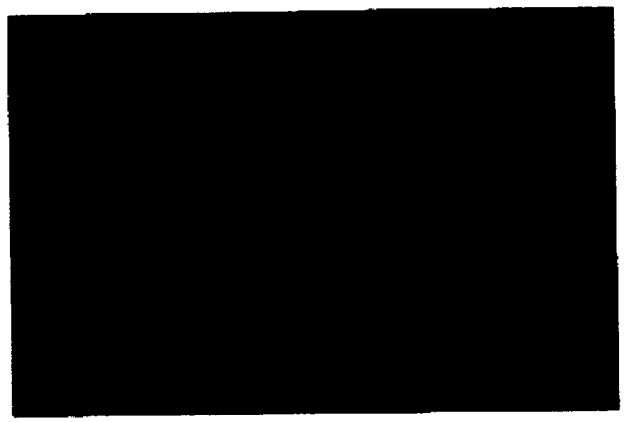
FIGS. 15A and 15B respectively illustrate experimental measured first derivative or slope images on the back surfaces of the sample plate of FIGS. 6A and 6B at two cut depth/thickness ratios (d/L) in accordance with the thermal imaging method for determining defect depth of the preferred embodiment.
Figure 15B:

FIGS. 14A, 14B and 14C and FIGS. 15A and 15B respectively illustrate experimental measured first derivative or slope images on the front and back surfaces of the sample plate 600 at multiple cut depth/thickness ratios (d/L) in accordance with the thermal imaging method for determining defect depth of the preferred embodiment. FIGS. 14A, 14B and 14C shows the 2D $(-\partial T/\partial x)T_m$ images for the front surfaces with cracks d/L=0.25, 0.5, and 0.75. FIGS. 15A and 15B for the back surfaces of steel plates with cracks d/L=0.5, and 0.75.

Figure 16A:
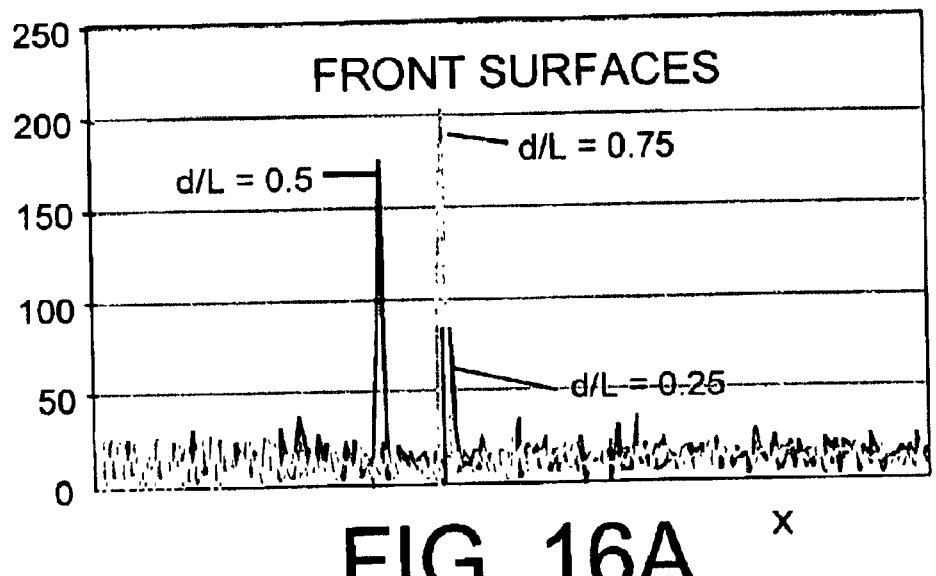
FIGS. 16A and 16B respectively illustrate experimental measured first derivative or slope profiles on the front surfaces of the sample plate of FIGS. 6A and 6B at two cut depth/thickness ratios (d/L) in accordance with the thermal imaging method for determining defect depth of the preferred embodiment.
Figure 16B:
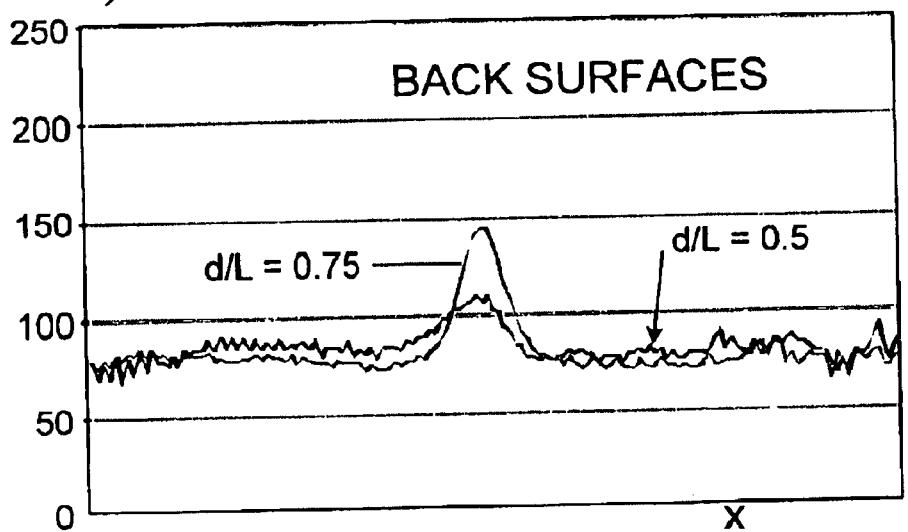

FIGS. 16A and 16B respectively illustrate experimental measured first derivative or slope profiles on the front surfaces of the sample plate at cut depth/thickness ratios (d/L) or cracks d/L=0.5, and 0.75 in accordance with the thermal imaging method for determining defect depth of the preferred embodiment. The measured $(-\partial T/\partial x)T_m$ profiles are plotted in FIGS. 16A and 16B.

Having reference to FIGS. 17, 18A, 18B, 18C, 19A, 19B, 20A, and 20B, additional data are provided by applying the method of the invention to detect normal and angled cracks in advanced ceramic-matrix-composite (CMC) materials. CMC materials are becoming widely utilized in high temperature applications such as in engines. There are typically two CMC materials that typically are encountered, one made of oxide fibers and oxide matrix, e.g., $Al_2O_3/Al_2O_3$, and the other of non-oxide material such as SiC/SiC. The oxide CMC material usually has lower thermal diffusivity (as low as 1 mm$^2$/s compared with typical value of >10 mm$^2$/s for steel) and, therefore, could be more difficult for crack detection. The non-oxide materials typically have higher diffusivity comparable to that of steel and should be easier for crack detection. The following analysis and experiments were conducted on oxide CMC.

The heat conduction equation of Equation 1 can be rearranged to:

$$\frac{\partial T}{\partial \tau} = \frac{\partial^2 T}{\partial x^2}, \quad (1a)$$

where $\tau=\alpha t$, a new time scale. It is apparent that Equation 1a is not dependent on material properties and, therefore, indicates that the sensitivity for detecting normal and angled cracks should be the same for all materials. The material dependent term is lumped into the time scale that is relevant to the duration of test. For example, if a test duration of 5 seconds is adequate for a material with $\alpha=10$ mm$^2$/s, the test duration should become 50 seconds to produce a result of same sensitivity for a material with $\alpha=1$ mm$^2$/s. Based on this observation, numerical simulations using the COMMIX code were performed for oxide CMC specimens ($\alpha=1$ mm$^2$/s) with normal and angled cracks of depths d/L=0.25, 0.5, and 0.75. With adjusted time scale, the results of these numerical simulations are exactly those as presented in FIGS. 8A, 8B, 8C, 9A, 9B, 9C, 10A and 10B.

Figure 17:
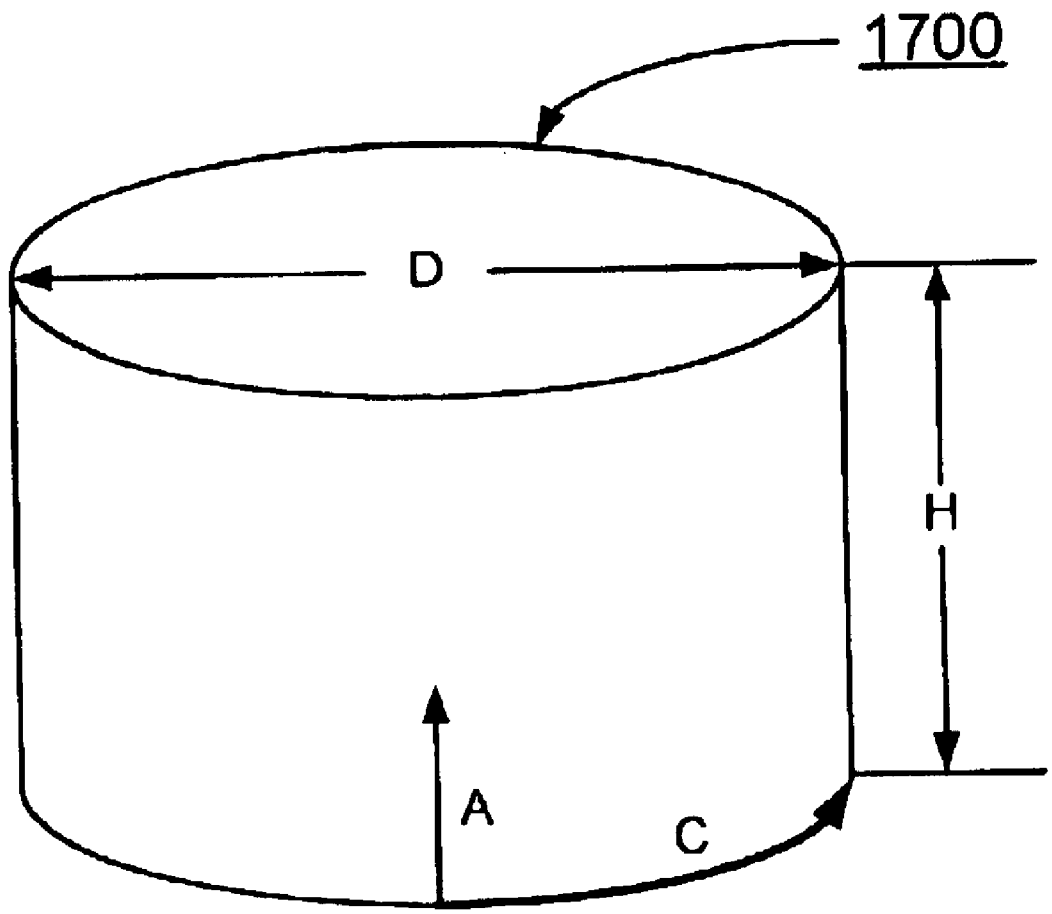
FIG. 17 is a diagram illustrating an oxide ceramic-matrix-composite (CMC) liner of cylindrical shape.

Referring to FIG. 17, there is shown an oxide ceramic-matrix-composite (CMC) liner of cylindrical shape generally designated by 1700 having a diameter indicated by an arrow labeled D and a height indicated by an arrow labeled H. An arrow labeled A indicates a central longitudinal axis or axial direction. An arrow labeled C indicates a circumferential direction.

Experiments were conducted to detect real cracks in an $Al_2O_3/Al_2O_3$ CMC liner. The tested liner 1700 is of cylindrical shape with a diameter of 200 mm (8 inches), axial length of 200 mm (8 inches), and wall thickness of 3 mm, as illustrated in FIG. 17. There are three normal cracks extending along the whole length of the axis, and they are identified as Cracks A, B, and C. Crack A is most severe, as it is visible from both inside and outside surfaces of the liner, see FIGS. 18A and 18B. Cracks B and C are seen only on inside surface of the liner with crack B shown in FIG. 19A, and crack C is the least severe because it is barely visible on the inside surface shown in FIG. 20A.

The experimental setup for testing the liner 1700 included a commercial light unit that contains a 500-Watts lamp as the constant heat source 106. A rectangular window (30 mm×120 mm) is placed between the light unit and the liner, with the long dimension of the window aligned to the liner longitudinal axis. After power-on the light unit, the radiation heat will generate uniform heat conduction in the liner's circumferential direction that is perpendicular to the cracks. The infrared camera 108 is placed to image the liner's outside surface. At each crack, three imaging tests were performed, each covering an area about ⅓ of the axial length. The complete image of each detected crack is composed from these three sectional images. With this setup, the Crack A is considered as a surface-breaking crack, and Cracks B and C are subsurface cracks.

Figure 18A:
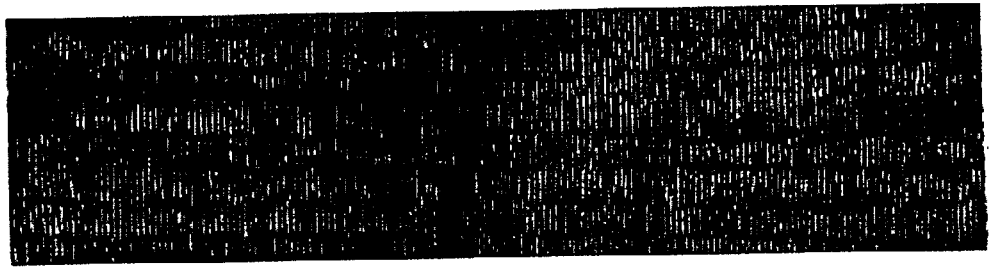
FIGS. 18A, 18B and 18C respectively illustrate a first crack as seen on an inside surface and an outside surface of the oxide CMC liner of FIG. 17, and a measured first derivative or slope image of the illustrated crack of FIGS. 18A, 18B in accordance with the thermal imaging method for determining defect depth of the preferred embodiment.
Figure 18B:
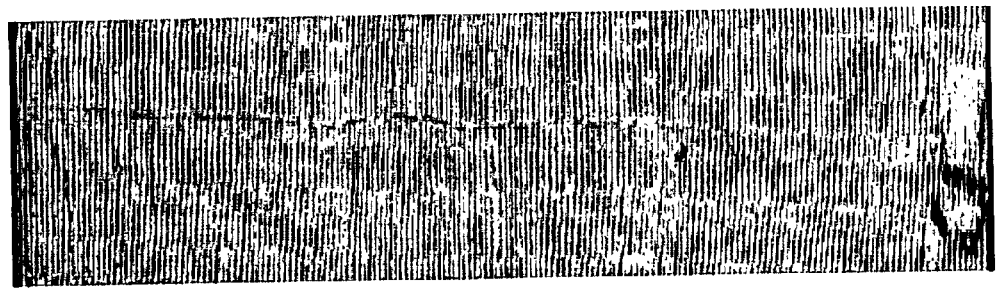
Figure 18C:
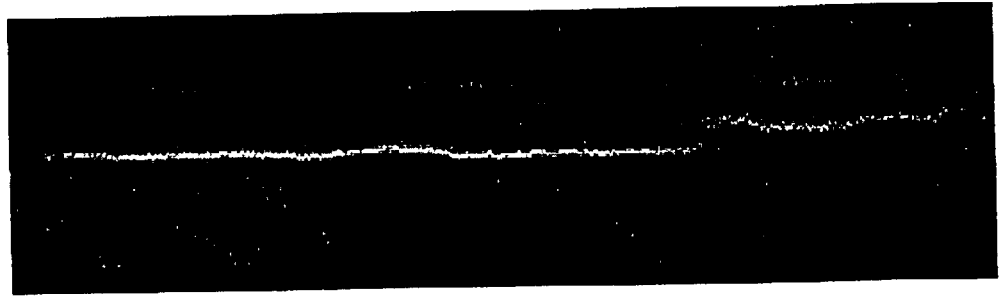

FIGS. 18A, 18B respectively illustrate the first crack A as seen on an inside surface and an outside surface of the oxide CMC liner 1700. FIG. 18C illustrates a measured first derivative or slope image of the illustrated crack of FIGS. 18A, 18B in accordance with the thermal imaging method for determining defect depth of the preferred embodiment.

Figure 19A:
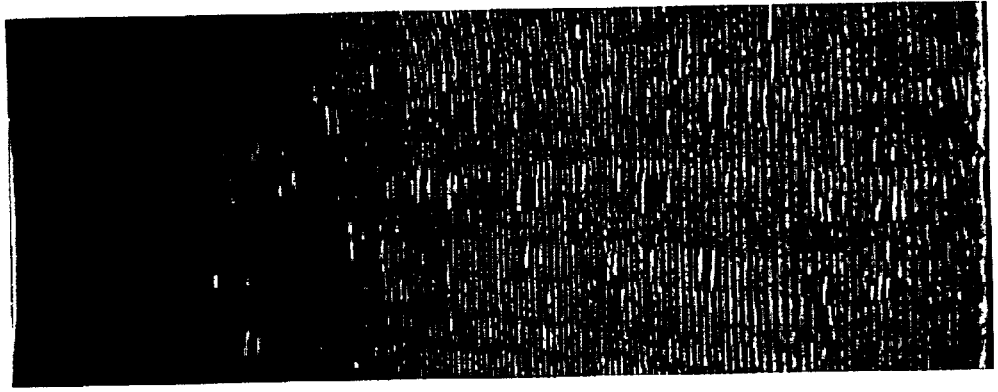
FIGS. 19A and 19B respectively illustrate a second crack as seen on an inside surface of the oxide CMC liner of FIG. 17, and a measured first derivative or slope image of the illustrated crack of FIG. 19A in accordance with the thermal imaging method for determining defect depth of the preferred embodiment.
Figure 19B:

FIGS. 19A and 19B respectively illustrate another crack B as seen on an inside surface of the oxide CMC liner 1700 and a measured first derivative or slope 2D $(-\partial T/\partial x)T_m$ image of the illustrated crack in accordance with the thermal imaging method for determining defect depth of the preferred embodiment.

Figure 20A:
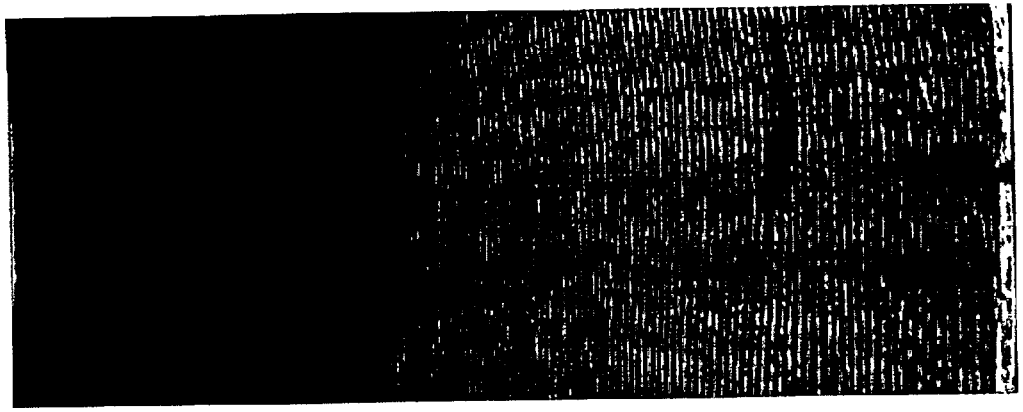
FIGS. 20A and 20B respectively illustrate a third crack as seen on an inside surface of the oxide CMC liner of FIG. 17, and a measured first derivative or slope image of the illustrated crack of FIG. 19A in accordance with the thermal imaging method for determining defect depth of the preferred embodiment.
Figure 20B:

FIGS. 20A and 20B respectively illustrate another crack C as seen on an inside surface of the oxide CMC liner 1700 and a measured first derivative or slope 2D $(-\partial T/\partial x)/T_m$ image of the illustrated crack in accordance with the thermal imaging method for determining defect depth of the preferred embodiment.

It should be pointed out that the liner 1700 was made in an early stage of CMC development, so it has non-uniform material and very rough surfaces which contribute to all the background variations or noise in the 2D $(-\partial T/\partial x)T_m$ images in FIGS. 18C, 19B and 20B. Even with this poor sample, the new method of the present invention can still detect all cracks with high sensitivities.

While the present invention has been described with reference to the details of the embodiments of the invention shown in the drawing, these details are not intended to limit the scope of the invention as claimed in the appended claims.

What is claimed is:

1. A method for detecting normal and angled cracks on or beneath a sample surface using infrared thermal imaging where the crack plane is perpendicular or angled to an imaged surface of the sample comprising the steps of:

providing a constant heating source for heating a section of the sample to produce a lateral heat transfer through the sample;

providing an infrared camera positioned near one side of the sample for receiving thermal image data resulting from the lateral heat transfer through the sample;

utilizing a data acquisition and processing computer for acquiring and differentiation processing thermal image data from said infrared camera for generating a two-dimensional image to detect the normal and angled cracks.

2. A method for detecting normal and angled cracks on or beneath a sample surface using infrared thermal imaging as recited in claim 1 wherein the step of utilizing said data acquisition and processing computer for acquiring and for differentiation processing thermal image data from said infrared camera includes the step of calculating first derivative slope image curves represented by $-\partial T/\partial x$, where T represents temperature and x represents distance relative to said constant heating source.

3. A method for detecting normal and angled cracks on or beneath a sample surface using infrared thermal imaging as recited in claim 2 wherein the step of calculating said first derivative slope image curves represented by $-\partial T/\partial x$ includes with an x-y plane of sample surface for said received thermal image data resulting from the lateral heat transfer through the sample, calculating each said first derivative slope image curves at all x-lines at each y=constant lines to form a two-dimensional $-\partial T/\partial x$ image; said two-dimensional $-\partial T/\partial x$ image including all normal and angled cracks including open cracks having crack surfaces separated by a gap and subsurface cracks in the sample.

4. A method for detecting normal and angled cracks on or beneath a sample surface using infrared thermal imaging as recited in claim 1 wherein the step of utilizing said data acquisition and processing computer for acquiring and for differentiation processing thermal image data from said infrared camera includes the step of calculating second derivative diffusivity images represented by $(\partial T/\partial t)/(\partial^2 T/\partial x^2)$.

5. A method for detecting normal and angled cracks on or beneath a sample surface using infrared thermal imaging as recited in claim 1 wherein the sample is formed of selected one of metallic materials, ceramic materials and composite materials.

6. Apparatus for detecting normal and angled cracks on or beneath a sample surface using infrared thermal imaging where the crack plane is perpendicular to imaged surface of the sample comprising:

a constant heating source for heating a section of the sample to produce a lateral heat transfer through the sample;

an infrared camera positioned near one side of the sample for receiving thermal image data resulting from the lateral heat transfer through the sample; and a data acquisition and processing computer for acquiring and differentiation processing thermal image data from said infrared camera for generating a two-dimensional image to detect the normal and angled cracks.

7. Apparatus for detecting normal and angled cracks on or beneath a sample surface using infrared thermal imaging as recited in claim 6 wherein said data acquisition and processing computer for acquiring and for differentiation processing thermal image data from said infrared camera includes calculating first derivative slope image curves represented by $-\partial T/\partial x$, where T represents temperature and x represents distance relative to said constant heating source.

8. Apparatus for detecting normal and angled cracks on or beneath a sample surface using infrared thermal imaging as recited in claim 7 wherein said infrared camera includes an array of infrared sensors, each of said infrared sensors detecting thermal image data.

9. Apparatus for detecting normal and angled cracks on or beneath a sample surface using infrared thermal imaging as recited in claim 8 wherein said detected thermal image data from each row of said array of infrared sensors is differentiation processed for generating each said two-dimensional image to detect the normal and angled cracks.

10. Apparatus for detecting normal and angled cracks on or beneath a sample surface using infrared thermal imaging as recited in claim 7 further includes the step of calculating second derivative diffusivity images represented by $(\partial T/\partial t)/(\partial^2 T/\partial x^2)$.

11. Apparatus for detecting normal and angled cracks on or beneath a sample surface using infrared thermal imaging as recited in claim 6 wherein said sample is formed of selected one or more of metallic materials and ceramic materials.

12. Apparatus for detecting normal and angled cracks on or beneath a sample surface using infrared thermal imaging as recited in claim 6 wherein said constant heating source includes a resistor heating element and a heat flux unit.

13. Apparatus for detecting normal and angled cracks on or beneath a sample surface using infrared thermal imaging as recited in claim 6 wherein said infrared camera includes an array of 256×256 infrared sensors.

14. Apparatus for detecting normal and angled cracks on or beneath a sample surface using infrared thermal imaging as recited in claim 6 wherein said generated two-dimensional image to detect the normal and angled cracks provides information relative to both position and dimensions of detected normal and angled cracks.

* * * * *